(12) United States Patent
Sepper et al.

(10) Patent No.: US 11,571,451 B1
(45) Date of Patent: Feb. 7, 2023

(54) PHYTOTHERAPEUTIC PRODUCT FOR CORRECTION OF SYMPTOM-COMPLEX OF FIBROCYSTIC CHANGES OF MAMMARY GLAND

(71) Applicants: Alexander Sepper, New York, NY (US); Dennis Tubian, New York, NY (US); John Navi, New York, NY (US)

(72) Inventors: Alexander Sepper, New York, NY (US); Dennis Tubian, New York, NY (US); John Navi, New York, NY (US)

(*) Notice: Subject to any disclaimer, the term of this patent is extended or adjusted under 35 U.S.C. 154(b) by 15 days.

(21) Appl. No.: 17/839,089

(22) Filed: Jun. 13, 2022

(51) Int. Cl.
| | |
|---|---|
| A61K 36/233 | (2006.01) |
| A61K 36/232 | (2006.01) |
| A61K 36/53 | (2006.01) |
| A61K 36/537 | (2006.01) |
| A61K 47/34 | (2017.01) |
| A61K 47/40 | (2006.01) |
| A61K 47/42 | (2017.01) |
| A61K 47/36 | (2006.01) |
| A61K 45/06 | (2006.01) |

(52) U.S. Cl.
CPC .......... *A61K 36/233* (2013.01); *A61K 36/232* (2013.01); *A61K 36/53* (2013.01); *A61K 36/537* (2013.01); *A61K 45/06* (2013.01); *A61K 47/34* (2013.01); *A61K 47/36* (2013.01); *A61K 47/40* (2013.01); *A61K 47/42* (2013.01)

(58) Field of Classification Search
None
See application file for complete search history.

(56) References Cited

FOREIGN PATENT DOCUMENTS

WO    WO-9532723 A1 * 12/1995 ........... A61K 36/185

* cited by examiner

*Primary Examiner* — Melissa S Mercier

(57) ABSTRACT

A phytotherapeutic product for treatment of fibrocystic changes of mammary gland.

11 Claims, 3 Drawing Sheets

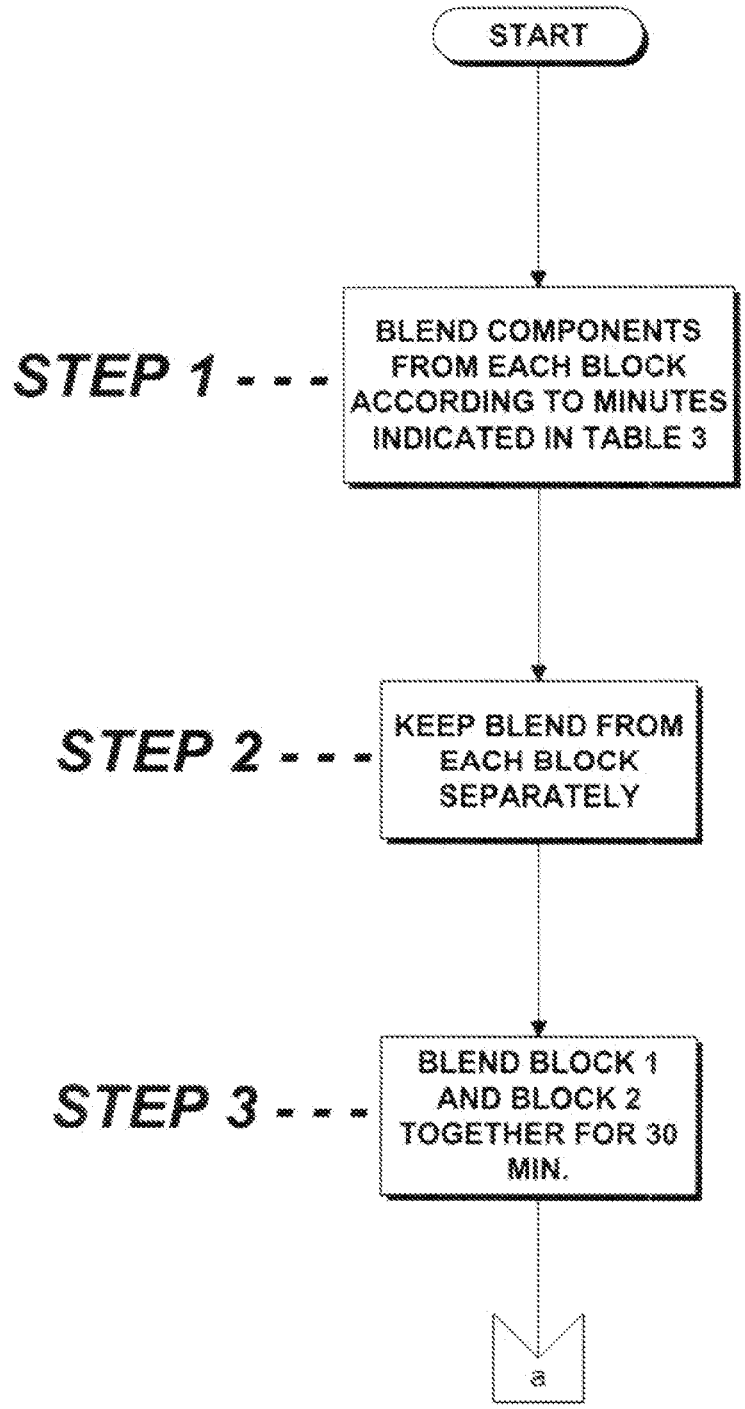
FIG. 1-A

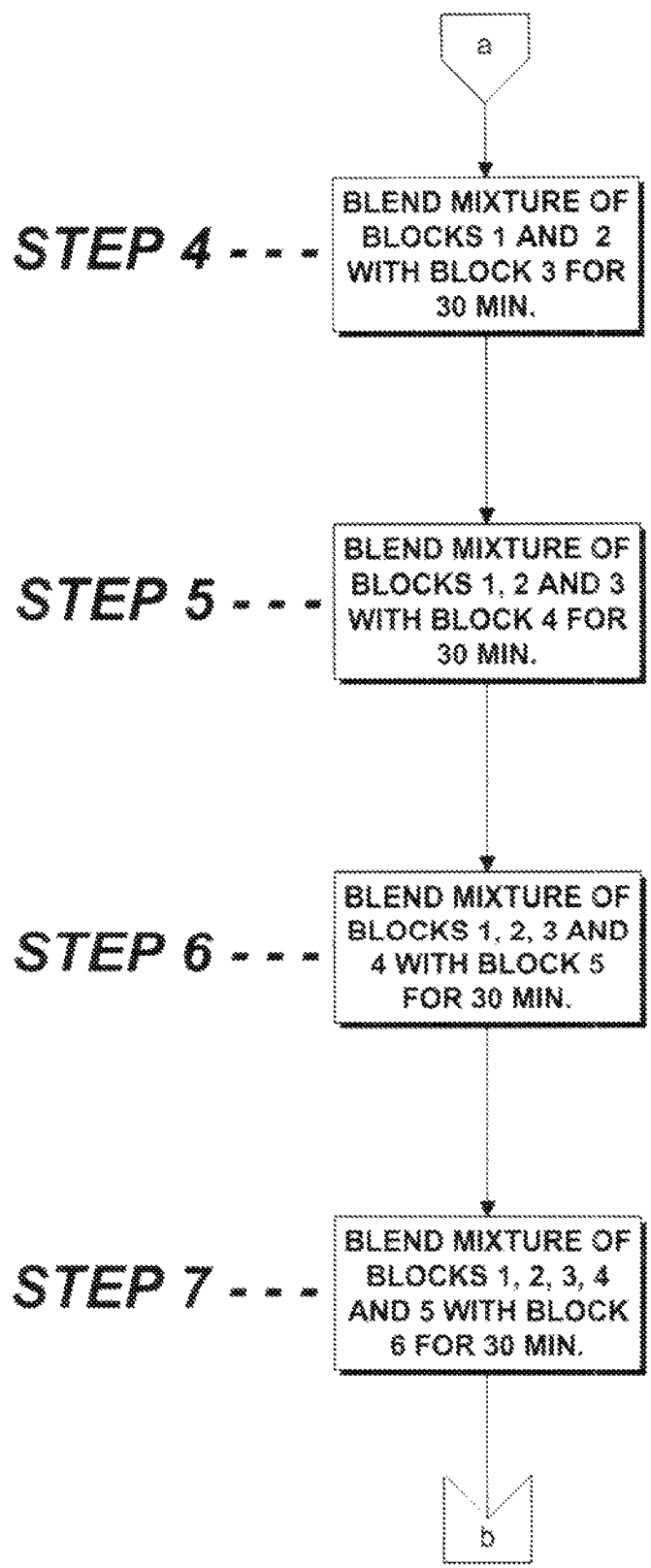
FIG. 1-B

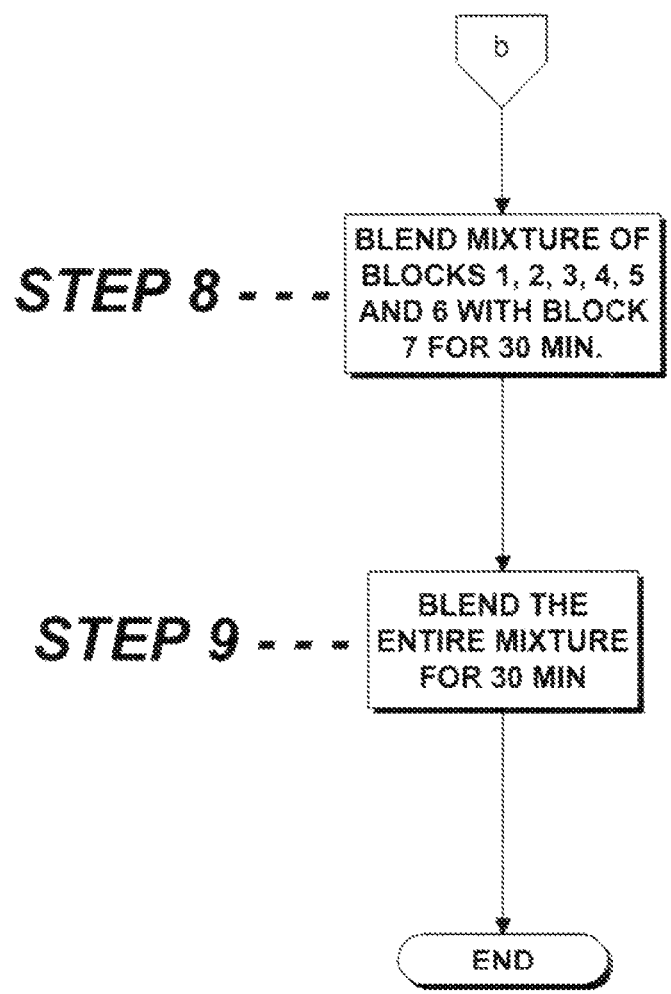
FIG. 1-C

PHYTOTHERAPEUTIC PRODUCT FOR CORRECTION OF SYMPTOM-COMPLEX OF FIBROCYSTIC CHANGES OF MAMMARY GLAND

FIELD OF THE INVENTION

The invention relates to a phytotherapeutic product, and more particularly, the invention relates to a phytotherapeutic product for correction of symptom-complex of fibrocystic changes of mammary gland.

BACKGROUND OF THE INVENTION

Numerous innovations for mammary gland-related treatments have been provided in the prior art, which are adapted to be used. Furthermore, even though these innovations may be suitable for the specific individual purposes to which they address, nevertheless, they would not be suitable for the purposes of the invention as heretofore described. None of the prior art compositions provide the benefits of the the invention providing a phytotherapeutic product for correction of symptom-complex of fibrocystic changes of mammary gland.

BRIEF DESCRIPTION OF THE INVENTION

An object of the invention is to provide a phytotherapeutic product for correction of symptom-complex of fibrocystic changes of mammary gland, which avoids the disadvantages of the prior art. The product encompasses formulations (particularly liquid formulations) that can be adapted for oral administration.

Another object of the invention is to provide a phytotherapeutic product designed according to the pathogenetic principle of selection of herbal components. In one preferred embodiment, the drug formulation of the invention contains 18 herbal components acting on the following pathogenetic mechanisms:

a group of ingredients aimed at correcting endocrine balance;

a group of ingredients with an immunomodulatory effect;

a group of ingredients with antidepressant and sedative effects;

a group of ingredients with a direct effect on the nodules of the mammary gland;

a group of ingredients normalizing the function of the thyroid gland;

a group of ingredients for correcting detoxification function of the liver; and a group of ingredients with anti-inflammatory action.

The product consists of two parts:

1) Delivery System sub-formulation—32%

2) Active Herbal Extract sub-formulation—68%

The phytotherapeutic product is formulated with the above components to provide a liquid formulation for oral administration.

The invention will be best understood from the following description of the invention when read and understood in connection with the accompanying FIGURES of the tables and drawing(s).

BRIEF DESCRIPTION OF THE DRAWING

The FIGURES of the drawing are briefly described as follows:

FIGS. 1A-1C is a diagrammatic flowchart of the method of making the phytotherapeutic product of the invention for correction of symptom-complex of fibrocystic changes of mammary gland.

DETAILED DESCRIPTION OF THE INVENTION

The invention encompasses a phytotherapeutic product is formulated to be a liquid formulation for oral administration. The invention is a phytotherapeutic product for the correction of symptom-complex of fibrocystic changes of the mammary gland, which provides and contributes to:

Elimination of pain syndrome; Significant reduction of swelling and tenderness of the mammary gland; significant decrease in focal nodularity of the breast; and decrease in degree of inflammatory reaction of the glandular tissue.

The invention is designed according to the pathogenetic principle of selection of herbal components. The product of the invention contains 18 herbal components acting on the following pathogenetic mechanisms:

A group of ingredients aimed at correcting endocrine balance;

A group of ingredients with immunomodulatory effect;

A group of ingredients with antidepressant and sedative effects;

A group of ingredients with direct effect on the nodules of the mammary gland;

A group of ingredients normalizing function of the thyroid gland;

A group of ingredients for correcting detoxification function of the liver; and

A group of ingredients with anti-inflammatory action.

In the table below, "Real Conc" refers to a concentration of the appropriate ingredient in the formulation of product. "Produced" refers to the amount of product prepared in accordance with formulation. The algorithm allows order any amount of product for preparation.

Below is a table shows ingredient concentrations for delivery system sub-formulation.

| Delivery system sub-formulation - natural polymers | | | |
|---|---|---|---|
| INGREDIENT | Real conc. % wt/wt % | Produced (g) 100 | Conc. range % wt/wt |
| Distilled water | 83.87 | 83.87 | 65-92 |
| b-Cyclodextrine (HPBC) | 5.30 | 5.30 | 3.3-8.2 |
| Dextran | 2.20 | 2.20 | 0.8-4.4 |
| Albumin (Avian) | 2.60 | 2.60 | 0.8-4.4 |
| Chitosan water soluble | 1.20 | 1.20 | 0.6-4.2 |
| Polyethilene Glycol-400 (PEG-400) | 4.10 | 4.10 | 3.0-7.8 |
| Xanthan gum (XG) | 0.15 | 0.15 | 0.1-2.4 |
| Hyaluronic acid (HA) | 0.13 | 0.13 | 0.1-4.7 |
| e-Polylysin 25% solution | 0.45 | 0.45 | 0.2-8.1 |
| TOTAL | 100.00 | 100.00 | |

Preparation Procedure for Delivery System

The liquid formulation may be made by the following steps.

1. Dissolve b-Cyclodextrine (HPBC) in Distilled water at room temperature.

2. Mix to complete dissolution stirring at 200 rpm.

3. Add Dextran and Chitosan according to the formulation.

4. Mix to complete dissolution stirring at 200 rpm.

5. Add Albumin per the formulation.

6. Continue mixing for 40 min at low speed (stirring at 100 rpm).

7. Separately prepare Xanthan gum and Hyaluronic acid slurry in Polyethylene Glycol-400 in quantities as shown.

8. Add the Xanthan gum and Hyaluronic acid slurry to water solution of polymers.

9. Mix thoroughly 60 min at 200-250 rpm.

10. Add e-Polylysin 25% solution.

11. Check pH and adjust to pH 5.5.

12. This is the delivery system mixture—Store under refrigeration.

Active Herbal Extract Sub-Formulation

Note that normal commercially produced herbal extracts cannot be used in this product, because concentration of active agents is less than 1%. Each ingredient in this product is custom produced ready to use in the liquid formulation where the concentration of active ingredients is not less than 10%. Below is a table showing ingredient concentrations for the Active Herbal Extract sub-formulation. The Active Herbal Extract mixture is shown in seven different "blocks" or "batches" which will be combined using a specific method as disclosed herein.

| Active sub-formulation - liquid herbal extracts (18 Herbal Extracts) | | | |
|---|---|---|---|
| INGREDIENT | Real Conc. % wt/wt | Produced (g) 100 | Conc. Ranges % wt/wt |
| BLOCK 1 - NORMALIZATION OF ENDOCRINE BALANCE | | | |
| *Bupleurum falcatum*/Bupleeurum | 6.20 | 6.20 | 2.5-9.6 |
| *Angelica sinensis*/Dong quai | 6.20 | 6.20 | 2.3-9.7 |
| *Agnus Castus*/*Vitex*/Chasteberry, Chaste tree | 12.80 | 12.80 | 5.3-18.6 |
| Sage leaf | 6.20 | 6.20 | 2.1-8.9 |
| *Cimicifuga dahurica*/Cohosh | 6.20 | 6.20 | 2.4-9.3 |
| SUBTOTAL | | 37.60 | 37.60 |
| BLOCK 2 - ACTION ON BREAST LUMPS | | | |
| *Chelidonium majus*/Celandine | 6.30 | 6.30 | 3.2-8.7 |
| *Viscum album*/Mistletoe | 6.30 | 6.30 | 3.1-9.2 |
| *Artemisia vulgare*/Common mugwort | 4.50 | 4.50 | 1.2-6.6 |
| SUBTOTAL | | 17.10 | 17.10 |
| BLOCK 3 - IMMUNOMODULATION | | | |
| *Echinacea purpurea*/Echinacea | 3.00 | 3.00 | 0.8-4.6 |
| Mother Wort | 3.00 | 3.00 | 0.6-4.5 |
| *Eleuterococcus senticosus*/Siberian ginseng | 3.00 | 3.00 | 0.7-5.2 |
| SUBTOTAL | | 9.00 | 9.00 |
| BLOCK 4 - ACTION ON THYROID GLAND | | | |
| *Withania* (*Withania somnifera*)/Ashwagandha | 6.00 | 6.00 | 3.2-9.8 |
| SUBTOTAL | | 6.00 | 6.00 | 2.8-9.6 |
| BLOCK 5 - HEPATOPROTGECTIVE ACTION | | | |
| Rhodiola root | 4.50 | 4.50 | 1.1-8.2 |
| *Zea mais*/Corn | 4.50 | 4.50 | 1.7-8.3 |
| SUBTOTAL | | 9.00 | 9.00 |
| BLOCK 6 - SPASMOLYTIC ACTION | | | |
| *Hypericum perforatum*/St John's-wort | 4.70 | 4.70 | 2.2-7.6 |
| *Matricaria officinale*/Camomile | 4.60 | 4.60 | 2.1-8.9 |
| SUBTOTAL | | 9.30 | 9.30 |
| BLOCK 7 - ANTI-INFLAMMATORY ACTION | | | |
| *Plantago Major* L./Plantane | 6.00 | 6.00 | 1.3-7.9 |
| *Calendula Officinalis* L./Calendula | 6.00 | 6.00 | 1.6-8.8 |
| SUBTOTAL | | 12.00 | 12.00 |
| TOTAL | | 100.00 | 100.00 |

Xanthan Gum and Hyaluronic Acid may be added to the aqueous formulation of polymers Preparation Procedure for Active Sub-Formulation The ingredients above will be combined as follows.

Block 1—Normalization of Endocrine Balance

Add each ingredient for this Block according to the formulation.

Mix at low speed (150-200 rpm) for 40 min.

Keep the mixture separately in refrigerator.

Block 2—Action on Breast Lumps

Add each ingredient for this Block according to the formulation.

Mix at low speed (150-200 rpm) for 30 min.

Keep the mixture separately in refrigerator.

Block 3—Immunomodulation

Add each ingredient for this Block according to the formulation.

Mix at low speed (150-200 rpm) for 20 min.

Keep the mixture separately in refrigerator.

Block 4—Action on Thyroid Gland

Extracts for this block are ready for further production.

Keep them in refrigerator.

Block 5—Hepatoprotgective Action

Add each ingredient for this Block according to the formulation.

Mix at low speed (150-200 rpm) for 15 min.

Keep the mixture separately in refrigerator.

Block 6—Spasmolytic Action

Add each ingredient for this Block according to the formulation.

Mix at low speed (150-200 rpm) for 15 min.

Keep the mixture separately in refrigerator.

Block 7—Anti-Inflammatory Action

Add each ingredient for this Block according to the formulation.

Mix at low speed (150-200 rpm) for 15 min. Keep refrigerated.

Xanthan Gum and Hyaluronic Acid may be added to the aqueous formulation of polymers.

Each of the above blocks should be produced separately and refrigerated. Prior to mixing for final product formulation, each block should be removed from the refrigerator and maintained at room temperature for at least 20 minutes prior to mixing.

Final Product Formulation

Below is a table showing ingredient concentrations for the final liquid formulation

FINAL PRODUCT

| INGREDIENT | Real conc. % wt/wt | Produced (g) 100 | Conc Ranges % wt/wt |
|---|---|---|---|
| Delivery System | 32.00 | 32.00 | 16-67 |
| Herbal Mixture #1 (Block1) | 25.60 | 25.60 | 10-32 |
| Herbal Mixture #2 (Block2) | 11.60 | 11.60 | 5-18 |
| Herbal Mixture #3 (Block3) | 6.10 | 6.10 | 2.3-8.6 |
| Herbal Mixture #4 (Block4) | 4.10 | 4.10 | 1.2-7.9 |
| Herbal Mixture #5 (Block5) | 6.10 | 6.10 | 1.2-8.7 |
| Herbal Mixture #6 (Block6) | 6.30 | 6.30 | 1.8-9.6 |
| Herbal Mixture #7 (Block7) | 8.20 | 8.20 | 1.2-12.0 |
| TOTAL | 100.00 | 100.00 | |

The final formulation product consists of two parts:
1) Delivery System sub-formulation—32% wt/wt
2) Active Herbal Extract sub-formulation—68% wt/wt Xanthan Gum and Hyaluronic Acid may be added to the aqueous formulation of polymers.

Preparation Procedure for Final Liquid Formulation

1. Remove all delivery system sub-formulation blocks/batches from fridge and leave at room temp. for about 20 mins.
2. Combine all delivery system sub-formulation blocks/batches and mix at low speed (150-200 rpm) for 10-30 min (usually 20-25 mins).
3. Add the active herbal extract sub-formulation in order of block number, one after another, mixing for 10-12 min after the addition of each block.
4. Homogenize using a homogenizer (e.g., an Ultra Turax™ Homogenizer). Time of Homogenization depends on the volume of final product, for example between 1 and 20 mins, 3-12 mins, 4-8 mins, or 5-7 mins. During Homogenization maintain temperature between 35-36 Centigrade.
5. After homogenization, mix under low speed for 8 hours (for example from 2-16 hrs, 4-10 hrs, 6-8 hrs, for example for 4, 3, 4, 5, 6, 7, 8, 9, or 10 hrs+/−20%) to provide full combination of ingredients.
6. Check pH and adjust to about pH 5.5 (for example from 4.8 to 7.0, or 5.0 to 6.5, or 5.0 to 6.2).
7. This is e final formulation ready for encapsulation. Encapsulate of refrigerate formulation for later encapsulation.

Administration of the Formulation to a Subject

The regular regimen of taking this product is:
By mouth, 2× "0" size liquid capsules, 2×/day.
Each "0" size capsule contain 500 mg (0.5 g) of final liquid formulation.
Total dosage is 2 g of product per day.
Thus, a patient receives active ingredients in the following sub-component quantities:

NORMALIZATION OF ENDOCRINE BALANCE 0.512 g
  ACTION ON BREAST LUMPS 0.232 g
  IMMUNOMODULATION 0.122 g
  ACTION ON THYROID GLAND 0.082 g
  HEPATOPROTGECTIVE ACTION 0.122 g
  SPASMOLYTIC ACTION 0.126 g
  ANTI-INFLAMMATORY ACTION 0.164 g
  Total amount of all ingredients=1.360 g.

2000 mg is a total amount of ingredients including the delivery system

TABLE 1 illustrates an alternative formulation including *Pulsatilla pratensis* and *Conium maculatum* with ingredients with the range in % wt/wt.

| ACTIVE COMPONENT | Range in % wt/wt |
|---|---|
| Normalization of Endocrine Balance | |
| *Bupleurum falcatum*/Bupleeurum | 2.2-45.0 |
| *Agnus Castus* (*Vitex*) | 2.2-45.0 |
| *Pulsatilla pratensis* | 2.2-45.0 |
| *Cimicifuga dahurica* | 2.2-45.0 |
| *Conium maculatum* | 2.2-45.0 |
| *Rhodiola quadrifida* | 2.2-45.0 |
| Immunomodulation | |
| *Euphorbia fischeriana* | 2.2-45.0 |
| *Eleutherococcus senticosus* | 2.2-45.0 |
| *Echinacea purpurea* | 2.2-45.0 |
| Antidepressant and Sedative Action | |
| *Leonurus Quinquelobatus* Gilib. | 2.2-45.0 |
| *Hypericum perforatum* | 2.2-45.0 |
| Direct Action on Breast Lumps | |
| *Chelidonium majus* | 2.2-45.0 |
| *Viscum album* | 2.2-45.0 |
| *Artemisia vulgare* | 2.2-45.0 |
| Action on Thyroid Gland | |
| *Withania* (*Withania somnifera*) | 2.2-45.0 |
| Action on Liver and Gallbladder Disfunctions | |
| *Zea mais* | 2.2-45.0 |
| Anti-Inflammatory Action | |
| *Plantago Major* L. | 2.2-45.0 |
| *Calendula Officinalis* L./Calendula | 2.2-45.0 |

It is to be understood that in the compounding of the formulation, each ingredient is subjected to a grinding step and milled to a specific size given in micrometers (μm); and each ingredient is added to the mixture in a specific sequence as show in TABLE 2.

TABLE 2

| ACTIVE COMPONENT NAME | Particle Size in μm | Ingredient Number in Addition Sequence |
|---|---|---|
| *Bupleurum falcatum*/Bupleeurum | 2500 | 1 |
| *Agnus Castus* (*Vitex*) | 2500 | 2 |
| *Pulsatilla pratensis* | 2350 | 3 |
| *Cimicifuga dahurica* | 2250 | 4 |
| *Conium maculatum* | 2100 | 5 |
| *Rhodiola quadrifida* | 1900 | 6 |
| *Euphorbia fischeriana* | 1700 | 7 |
| *Eleutherococcus senticosus* | 1700 | 8 |
| *Echinacea purpurea* | 1500 | 9 |
| *Leonurus Quinquelobatus* Gilib. | 1500 | 10 |
| *Hypericum perforatum* | 1200 | 11 |
| *Chelidonium majus* | 1200 | 12 |
| *Viscum album* | 1100 | 13 |
| *Artemisia vulgare* | 1100 | 14 |
| *Withania* (*Withania somnifera*) | 1100 | 15 |
| *Zea mais* | 1000 | 16 |
| *Plantago Major* L. | 1000 | 17 |
| *Calendula Officinalis* L./Calendula | 1000 | 18 |

Method of Making the Phytotherapeutic Product for Correction of Symptom-Complex of Fibrocystic Changes of Mammary Gland The method of making the phytotherapeutic product for correction of symptom-complex of fibrocystic changes of mammary gland can be seen in FIGS. 1A-1C.

step 1: blend components of each batch (or "block") for time shown in table 3;
step 2: keep blend from each block separately;
step 3: blend block 1 and block 2 together for 30 min.;
step 4: blend mixture of blocks 1 and 2 with block 3 for 30 min.;
step 5: blend mixture of blocks 1, 2 and 3 with block 4 for 30 min.;
step 6: blend mixture of blocks 1, 2, 3 and 4 with block 5 for 30 min.;
step 7: blend mixture of blocks 1, 2, 3, 4 and 5 with block 6 for 30 min.;
step 8: blend mixture of blocks 1, 2, 3, 4, 5 and 6 with block 7 for 30 min.; and
step 9: blend the entire mixture for 30 min.

Specific Active Ingredients in the Formulation Embodiment

The invention encompasses a phytotherapeutic compounds comprising a herbal liquid extract (Castain, $C_{19}H_{18}O_8$) of Agnus Castus incorporated in the polymeric delivery system. The main action of Castain ($C_{19}H_{18}O_8$) is the normalization of estrogen hormone imbalance in women organism as well as elimination of the concomitant chronic inflammatory process. Thus, it contributes to the positive dynamics of reversing pathological symptom complex of fibro-cystic condition of the breast.

Castain promotes the following:
fast elimination of mastalgia, pain syndrome and tenderness accompanying fibro-cystic disease.
decrease and in most cases complete resorption of breast lumpiness.
significant decrease of serous discharge from nipple.
fast improvement and elimination of menstrual discomfort.
normalization of psychological discomfort accompanying breast fibro-cystic disease Some Aspects of Extracts Processing Technology There are several variables that can change the product outcome:
1. The herb quality.
a) The organic material was ordered from the same supplier.
b) Herbs vary wildly from season to season, from growing area or even availability, which means sometimes we are forced to buy what we can get, not necessarily the best. It can help if you have access to a decent lab and look for active peaks of various herb constituents, then buy accordingly, but this is a big deal to setup. The only herb product supplier that does this is Australia's Medi-Herb.
c) Also, it implies that the herbs' actions are determined by a relatively few active constituents.
2. The processing of the herbs before extraction.
a) Their ages since harvest.
b) The degree that the processed herb absorbs water.
c) The grinding and particle size. As the particle size decreases, the efficiency of the extraction process increases, but at the expense of additional pressure required to percolate. But if the particle size is larger and the solvent residence on the column is shorter, the extraction is not as good.
3. The solvent composition.
a) Ideally, the solvent should be optimized for each herb formula. Typically, it is an alcohol:water blend. It is possible to use glycer in which has a similar solvent characteristics as alcohol to increase the non-aqueous portion of the blend. Also, it is not taxed and thus actually less expensive than taxed alcohol. Also, glycer in helps keep the herb extract from forming precipitates overtime and for some of the bitter herbs, its sweetness will make the extract more palatable.
4. If extracts are done at scale, then that company probably buys non-taxed alcohol. To do this there is a ATF permit, but the fee is steep and would have to use at least 55 gallons of alcohol per year to make it worthwhile. Alcohol itself is cheap; the tax is outrageous. The advantage of using cheap alcohol is that one can optimize the percolation process better. The solvent that comed off first is the most concentrated. One can test the percolate concentration and determine when to stop the solvent flow and then skip the hydraulic press step that resorts to use the solvent most efficiently. This is a time saver.

General Disclosures

This specification incorporates by reference all documents referred to herein and all documents filed concurrently with this specification or filed previously in connection with this application, including but not limited to such documents which are open to public inspection with this specification. All numerical quantities mentioned herein include quantities that may be plus or minus 20% of the stated amount in every case, including where percentages are mentioned. As used in this specification, the singular forms "a, an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. For example, a composition "comprising" (or "which comprises") ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example, "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). When, in this specification, a range is given as "(a first number) to (a second number)" or "(a first number)-(a second number)", this means a range whose lower limit is the first number and whose upper limit is the second number. For example, "from 40 to 70 microns" or "40-70 microns" means a range whose lower limit is 40 microns, and whose upper limit is 70 microns.

When discussing the amount of a compound in a final LIQUID formulation, we may use the relative units of Percent Volume (v/v). Typically, percent volume written as '% Vol' or 'Volume percent' or 'volume/volume percent' or 'v/v %'. This term is used when preparing solutions of liquids. Volume percent is defined as: v/v %=[(volume of solute)/(volume of solution)]×100%. Note that volume percent is relative to the volume of solution, not the volume of solvent. For example, wine is about 12% v/v ethanol. This means there is 12 ml ethanol for every 100 ml of wine. It is important to realize liquid and gas volumes are not necessarily additive. If you mix 12 ml of ethanol and 100 ml of wine, you will get less than 112 ml of solution.

Alternatively, in a liquid formulation, quantities can be given in terms of relative percent concentration by weight of solute in a solution by volume (sometimes given as the relative units wt/vol % or % wt/vol or wt/vol or wt/v or w/v). To determine the weight percent of a solution, divide the mass of solute by mass of the solution (solute and solvent together) and multiply by 100 to obtain percent. The percent by weight formula=gram of solute/100 g of solution.

Quantities in a solid formulation are given wt/wt %, also called weight fraction, sometimes shown as wt/wt or % wt/wt or wt/wt %.

Alternatively, and as frequently used in this disclosure, any mixtures such as solids in liquids, liquid in liquid and solids mixed with solids can also be expressed as % wt/wt. The weight of water is generally about 1 g/ml, so wt/vol and wt/wt is often similar or the same for a generally aqueous solution.

The term 'compounding' in this disclosure related to mixing one or more ingredients to provide a pharmaceutical preparation, i.e. a preparation designed to elicit a physiological effect.

All particle sizes are given in micrometers (μm), with any given size generally encompassing sizes+/−10% or +/−20% or +/−30% or (+/−20%)+/−40%.

Impressions

It will be understood that each of the elements described above or two or more together may also find a useful application in other types of constructions differing from the types described above.

While the invention have been illustrated and described as embodied in a phytotherapeutic product for correction of symptom-complex of fibrocystic changes of mammary gland, nevertheless, they are not limited to the details shown, since it will be understood that various omissions, modifications, substitutions, and changes in the forms and details of the invention illustrated and their operation can be made by those skilled in the art without departing in any way from the spirit of the invention.

Without further analysis, the foregoing will so fully reveal the gist of the invention that others can by applying current knowledge readily adapt them for various applications without omitting features from the standpoint of prior art fairly constitute characteristics of the generic or specific aspects of the invention.

The invention claimed is:

1. A phytotherapeutic formulation adapted for oral administration for treating fibrocystic changes of mammary gland, the formulation comprising: a delivery sub-formulation which is 32% by weight of the final formulation, combined with an active herbal extract sub-formulation which is 68% by weight of the final formulation,
wherein the delivery sub-formulation comprises the following components:
b-Cyclodextrine,
dextran,
albumin,
chitosan,
polyethylene glycol-400,
xanthan gum,
hyaluronic acid,
E-Polylysin and
distilled water;
and wherein the active sub-formulation comprises the following components:
bupleurum falcatum,
angelica sinensis,
Agnus Castus (vitex),
sage leaf,
cimicifuga dahurica,
chelidonium majus,
viscum album,
artemisia vulgare,
echinacea purpurea,
mother wort,
eleutherococcussenticosus,
withaniasomnifera,
rhodiola root,
zeamais,
hypericum perforatum,
matricaria officinale,
plantago major L and
calendula officinalis L.

2. The phytotherapeutic formulation of claim 1 wherein the relative amount of the components expressed as % wt/wt as follows:
for the delivery sub-formulation:
b-cyclodextrine 5.30% of delivery sub-formulation
dextran 2.20% of delivery sub-formulation
albumin 2.60% of delivery sub-formulation
chitosan water soluble 1.20% of delivery sub-formulation
polyethilene glycol-400 4.10% of delivery sub-formulation
xanthan gum 0.15% of delivery sub-formulation
hyaluronic acid 0.13% of delivery sub-formulation
e-polylysin 0.45% of delivery sub-formulation and for the active sub-formulation:
bupleurum falcatum 6.20% of active sub-formulation
angelica sinensis 6.20% of active sub-formulation
Agnus Castus (vitex) 12.80% of active sub-formulation
sage leaf 6.20% of active sub-formulation
cimicifuga dahurica 6.20% of active sub-formulation
chelidonium majus 6.30% of active sub-formulation
viscum album 6.30% of active sub-formulation
artemisia vulgare 4.50% of active sub-formulation
echinacea purpurea 3.00% of active sub-formulation
mother wort 3.00% of active sub-formulation
eleutherococcussenticosus 3.00% of active sub-formulation
withaniasomnifera 6.00% of active sub-formulation
rhodiola root 4.50% of active sub-formulation
zeamais 4.50% of active sub-formulation
hypericum perforatum 4.70% of active sub-formulation
matricaria officinale 4.60% of active sub-formulation
plantago major L 6.00% of active sub-formulation, and
calendula officinalis L 6.00% of active sub-formulation.

3. A formulation of claim 1, formulated as a liquid for oral administration.

4. The formulation of claim 2 comprising the ingredients in final quantities expressed as % wt/wt,
agnus castus (vitex) 9.4
angelica sinensis 3.2
sage 3.6
cimicifuga dahurica 2.4
bupleurum falcatum 6.8
chelidonium majus 6.6
viscum album 6.6
artemisia vulgare 4.3
echinaceapurpurea 6.7
mother wort 6.9
siberian ginseng 3.3
withania 4.5
helychrisumarenarium 8.4
zeamais
rhodiola root 7.7
matricaria officinale 6.7
plantago major L 6.0, and
calendula officinalis L 5.2.

5. A product-by-process wherein the product is a phyto-therapeutic formulation for treating fibrocystic changes of mammary gland, and the formulation is made by a process of compounding ingredients comprising:
agnus castus (vitex)
angelica sinensis
sage
cimicifuga dahurica
bupleurum falcatum
chelidonium majus
viscum album
artemisia vulgare
echinaceapurpurea
mother wort
siberian ginseng
withania
helychrisumarenarium
zeamais
rhodiola root
matricaria officinale
plantago major L, and
calendula officinalis L.

6. The product-by-process of claim 5 further comprising mixing the components with a delivery system comprising the following:
Distilled water
b-Cyclodextrine
Dextran
Albumin
Chitosan water soluble
Polyethylene glycol-400
Xanthan gum
Hyaluronic acid
e-Polylysin.

7. The product-by-process of claim 6 wherein the ingredients are provided and processed in batches 1-7, and wherein the following ingredients are ground and/or blended together in individual batches each for a specific time, as follows:
batch 1
bupleurum falcatum
agnus castus,
pulsatilla pratensis,
cimicifuga dahurica,
conium maculatum, and
rhodiolaquadrifida are blended together for [20×(wkg×0.5)] min;
batch 2
euphorbia fischeriana,
eleutherococcussenticosus, and
echinacea purpurea are blended together for [20×(wkg×0.5)] min;
batch 3
leonurusquinquelobatusgilib, and
hypericum perforatum are blended together for [15×(wkg×0.5)] min;
batch 4
chelidonium majus,
viscum album, and
artemisia vulgare are blended together for [20×(wkg×0.5)] min;
batch 5
withaniasomnifera is ground for [10×(wkg×0.5)] min;
batch 6
zeamais is ground for [10×(wkg×0.5)] min; and
batch 7
plantago major L and
calendula officinalis L/calendula are blended for [15×(wkg×0.5)] minutes;
where Wkg is a total weight of each batch being blended, and wherein after grinding and/or blending of the batches, all batches are then mixed together to produce a formulation for treating fibrocystic changes of mammary gland.

8. The product-by-process of claim 7 the following steps are performed:
step 1: blend components of each batch for time shown in claim 6;
step 2: keep blends from each batch separately;
step 3: blend batch 1 and batch 2 together for 30 minutes;
step 4: blend mixture of batches 1 and 2 with batch 3 for 30 minutes;
step 5: blend mixture of batches 1, 2 and 3 with batch 4 for 30 minutes;
step 6: blend mixture of batches 1, 2, 3 and 4 with batch 5 for 30 minutes;
step 7: blend mixture of batches 1, 2, 3, 4 and 5 with batch 6 for 30 minutes;
step 8: blend mixture of batches 1, 2, 3, 4, 5 and 6 with batch 7 for 30 minutes; and
step 9: blend the entire mixture for 30 minutes.

9. The phytotherapeutic formulation of claim 1 further comprising pulsatilla pratensis and conium maculatum.

10. The formulation of claim 4 wherein the average particle size in μm of each ingredient is between 1000 μm and 2500 μm.

11. The product-by-process of claim 6 wherein, in the final formulation, the % wt/wt of the batches is:
Batch 1 32.00%
Batch 2 16.00%
Batch 3 13.8%
Batch 4 7.9%
Batch 5 8.5%
Batch 6 19.9%
Batch 7 5.9%.

* * * * *